United States Patent [19]

Yoshida et al.

[11] 4,007,179
[45] Feb. 8, 1977

[54] OXOINDANYLPROPIONIC ACIDS AND PROCESS FOR THE PREPARATION THEREOF

[75] Inventors: Norio Yoshida; Kiichiro Tanaka, both of Tokyo, Japan

[73] Assignee: Sankyo Company Limited, Tokyo, Japan

[22] Filed: Jan. 27, 1976

[21] Appl. No.: 652,727

[30] Foreign Application Priority Data

Feb. 19, 1975 Japan .............................. 50-20696

[52] U.S. Cl. .................. 260/247.2 R; 260/293.62; 260/501.1; 260/515 R; 260/515 P; 260/469; 424/248.53; 424/267; 424/308; 424/316

[51] Int. Cl.[2] ..................................... C07D 295/00

[58] Field of Search ............... 260/515 R, 247.2 R, 260/293.62, 501.1

[56] References Cited

UNITED STATES PATENTS

| | | | |
|---|---|---|---|
| 3,532,752 | 10/1970 | Shen et al. | 260/501.1 |
| 3,644,479 | 2/1972 | Juby et al. | 260/501.1 |
| 3,929,872 | 12/1975 | Cragoe, Jr. et al. | 260/515 R |
| 3,932,498 | 1/1976 | Shen et al. | 260/501.1 |

OTHER PUBLICATIONS

Rahman et al., Chem. Abst., vol. 78, 3990(u), 1973.
Yoshihira et al., Chem. Pharm. Bull., 19(7), 1491–1495 (1971).
Nambudiry et al., Chem. Abst., vol. 80, 121128(h)(74).
Huneck et al., Chem. Abst., vol. 71, 91132z (1969).

*Primary Examiner*—James O. Thomas, Jr.
*Assistant Examiner*—G. T. Breitenstein
*Attorney, Agent, or Firm*—Flynn & Frishauf

[57] ABSTRACT

An oxoindanylpropionic acid having the formula

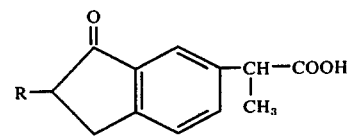

wherein R represents ethyl group or isopropyl group and a salt thereof is prepared by reacting a dicarboxylic acid having the formula

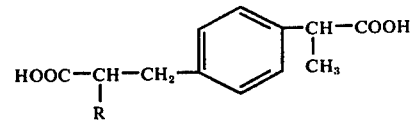

wherein R has the same meaning as defined above with a condensing agent, for example, sulfuric acid.

The oxoindanylpropionic acid is reduced to give the corresponding indanylpropionic acid which is useful as anti-inflammatory, analgesic and antipyretic agents.

5 Claims, No Drawings

OXOINDANYLPROPIONIC ACIDS AND PROCESS FOR THE PREPARATION THEREOF

This invention relates to a novel compound and a process for the preparation thereof.

More particularly it relates to an oxoindanylpropionic acid having the formula

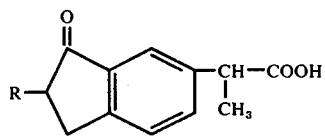

wherein R represents ethyl group or isopropyl group and a process for the preparation thereof.

Previously we have found that certain indanylpropionic acids exhibit high anti-inflammatory, analgesic and antipyretic activities and we have filed a patent application covering the indanylpropionic acid and the process for the preparation thereof [U.S. Pat. application Ser. No. 535,685].

As a result of subsequent investigations, we have found a more advantageous process for preparing the indanylpropionic acid.

It is thus an object of the present invention to provide an oxoindanylpropionic acid useful as an intermediate for the synthesis of the indanylpropionic acid having anti-inflammatory, analgesic and antipyretic activities.

It is another object of the present invention to provide a process for the preparation of such an oxoindanylpropionic acid.

It is a further object of this invention to provide an improved process for the preparation of such an indanylpropionic acid useful as anti-inflammatory, analgesic and antipyretic agents.

According to the present invention, the oxoindanylpropionic acid having the formula (I) can be prepared by reacting a dicarboxylic acid having the formula

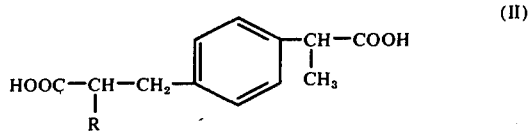

wherein R has the same meaning as defined above with a condensing agent.

In carrying out the process of this invention, the reaction can be conducted by adding the dicarboxylic acid to the condensing agent and heating the mixture usually at a temperature ranging from 50° to 120° C.

Representative examples of the condensing agent include a mineral acid, for example, polyphosphoric acid, sulfuric acid and hydrofluoric acid; phosphorus pentoxide - methanesulfonic acid; and a Lewis acid, for example, aluminum chloride and boron trifluoride ethyl etherate. The reaction period varies depending upon the reaction temperature, but generally it is about 1 – 5 hours. A solvent is generally not necessary to the reaction, since the condensing agent may serve as a solvent. However, in case where the Lewis acid is employed, it is preferable to employ a solvent which is usually employed in Friedel-Crafts reaction, for example, carbon disulfide and ligroin.

After completion of the reaction, the desired product (I) may be recovered from the reaction mixture by conventional means. For example, the reaction mixture is poured into ice-water and extracted with an appropriate organic solvent, e.g., ether. The extract is washed with water and dried. The solvent is distilled off from the extract to give the desired product. The product thus obtained may be, if necessary, purified by a usual method such as vacuum distillation and column chromatography. Alternatively, the desired product may be purified by recrystallization after formation of a salt with an organic amine, for exaple, piperidine, morpholine, triethylamine, dicyclohexylamine and dibenzylamine.

The starting material of the formula (II) is novel and can be prepared by the process shown in the following reaction scheme:

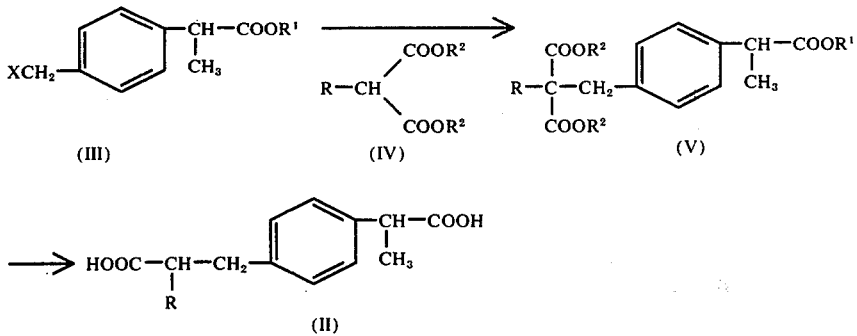

In the above reaction scheme, R has the same meaning as defined above, $R^1$ and $R^2$ represent an alkyl group having 1–4 carbon atoms and X represents chlorine a atom or bromine atom.

The process for the preparation of the compound having the formula (II), shown in the reaction scheme, will now be described below in detail.

The tricarboxylic acid ester (V) can be prepared by reacting the benzyl halide (III), which may be prepared by the method described by J. M. Maillard et al., in Chimie Therapeutique, vol. 8, 487 (1973), with the malonic acid ester (IV) in the presence of an alkali metal compound in an inert organic solvent.

Representative examples of the alkali metal compound include alkali metal alcoholates, e.g., sodium methoxide, sodium ethoxide, potassium tert-butoxide; alkali metal amides, e.g., sodium amide, potassium amide; and alkali metal hydrides, e.g., sodium hydride, potassium hydride. Preferable examples of the solvent include alcohols, e.g., methanol, ethanol, tert-butanol;

dialkyl alkanoic acid amides, e.g., dimethylformamide, dimethylacetamide; dimethyl sulfoxide; ethers, e.g., tetrahydrofuran, dioxane, 1,2-dimethoxyethane; and aromatic hydrocarbons, e.g., benzene, toluene and xylene. The reaction may be preferably carried out at 0°–50° C. for 1–5 hours. The product can be isolated from the reaction mixture by conventional means. For example, the mixture is poured into ice-water and made acidic by addition of an acid, e.g., hydrochloric acid, followed by extraction by an appropriate organic solvent. The extract is washed with water, dried and evaporated to dryness to give the desired product (V).

The dicarboxylic acid (II) can be prepared by subjecting the tricarboxylic acid ester (V) to hydrolysis and subsequent decarboxylation.

The hydrolysis may be carried out by contacting the compound (V) with an acid, e.g., hydrochloric acid, hydrobromic acid, sulfuric acid, or a base, e.g., sodium hydroxide, potassium hydroxide, in the presence of water. The reaction may be preferably conducted in water or an aqueous organic solvent, e.g., aqueous methanol, ethanol, n-propanol, ethylene glycol, diethylene glycol, dimethylformamide and dimethylacetamide solution. The reaction is carried out at a temperature ranging from room temperature to 110° C. for 1–12 hours. The product may be recovered by conventional means.

The decarboxylation may be conducted by heating the product obtained above at 100°–200° C. in the presence or absence of a solvent.

As the solvent, there may be employed dialkyl alkanoic acid amides, e.g., dimethylformamide, dimethylacetamide; and aromatic hydrocarbons, e.g., toluene, xylene, cymene. In case where the solvent is not employed, it is desirable to carry out the reaction under reduced pressure or in an inert gas, e.g., nitrogen gas in order to prevent occurrence of side reactions. The reaction period varies depending mainly upon the reaction temperature and the kind of the starting material, but generally it is about from 15 minutes to 3 hours. The reaction product (II) may be isolated from the reaction mixture by conventional means. For example, the solvent, if used, is distilled off and the residue is purified by recrystallization or column chromatography.

The oxoindanylpropionic acid (I) is reduced to give the indanylpropionic acid having the formula

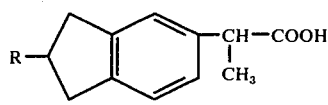

(VI)

wherein R has the same meaning as defined above.

The reduction can be conducted by contacting the compound (I) with a reducing agent in the presence of a solvent. As the reducing agent, there may be employed any conventional reducing agent which may convert a keto group to a methylene group without reducing a carboxyl group. Representative examples of the reducing agent include zinc amalgam — hydrochloric acid (Clemmensen reduction); hydrogen gas — a metal catalyst such as palladium on carbon, palladium oxide, platinum oxide, platinum black etc. (Catalytic reduction); hydrazine - a base such as sodium hydroxide, sodium ethoxide etc. (Wolff-Kischner reduction); an alkyl mercaptan such as 1,2-ethanedithiol and a desulfurization catalyst such as Raney nickel (Dithioacetal reduction) and the like. As the solvent, there is no particular limitation provided that it does not participate in the present reaction, but there may be preferably mentioned, for instance, water; an organic solvent such as an alcohol, e.g., methanol, ethanol, n-propanol, an ether, e.g., tetrahydrofuran, dioxan, 1,2-dimethoxyethane, a glycol, e.g., ethylene glycol, diethylene glycol, triethylene glycol, an organic acid such as acetic acid, propionic acid; and a mixture of the above solvent and water. In the present reaction, zinc amalgam — hydrochloric acid as well as hydrogen — a metal catalyst can be usually employed as the particularly preferable catalyst. Where hydrogen — a metal catalyst such as palladium on carbon are to be used, the reaction can be preferably effected by the addition of such an acid as sulfuric acid, perchloric acid, trifluoroacetic acid, p-toluenesulfonic acid according to a conventional manner. The reaction temperature is not particularly critical and the reaction may be usually effected at a temperature ranging from room temperature to about 200° C. In carrying out the catalytic reduction, the reaction may be effected at room temperature and under atmospheres pressure or about 2 – 3 atmospheric pressure and, in case of other reduction, the reaction may be preferably effected by heating at 70° – 200° C. The reaction period may vary depending upon the reaction temperature, the type of reducing agent employed and the like, but it is generally about 1 – 24 hours.

After completion of the reaction, the desired compound having the above formula (VI) may be recovered from the reaction mixture in a conventional manner. For instance, after completion of the reaction, insolubles are filtered off from the reaction mixture, which is then extracted with a suitable organic solvent. The resulting organic solvent layer is washed with water and dried. The solvent is distilled off from the extract to give the desired product. The desired product thus obtained may be further purified by a conventional technique such as recrystallization, vacuum distillation, column chromatography and the like, if necessary.

The indanylpropionic acid having the formula (VI) may be converted to a pharmaceutically acceptable salt by a conventional means. As the pharmaceutically acceptable salts, there may be mentioned salts of alkali or alkaline earth metals, e.g., sodium, potassium, calcium, aluminum salt, ammonium salt, or salts of organic bases, e.g., triethylamine, dicyclohexylamine, dibenzylamine, piperidine or N-ethylpiperidine.

Optical isomers of the compounds having the above general formula (I) or (VI) may be present owing to the presence of asymmetric carbon atoms. Then, if the compound having the above formula (I) or (VI) is obtained in the form of a mixture of optical isomers, each isomer may be isolated by conventional optical resolution. The compound having the above formula (I) or (VI) is disclosed herein with a single formula, but it is intended to include an optical isomer or a mixture thereof and not to limit the scope of this invention.

All of the compounds having the above formula (VI) are confirmed by pharmacological tests to show prominent anti-inflammatory, analgesic and antipyretic activities, and results of such pharmacological tests are exemplified hereinbelow.

| Drug | ID₅₀ (mg/kg p.o.) Anti-inflammatory | Analgesic | Antipyretic |
|---|---|---|---|
| 2-(2-Ethylindan-5-yl)propionic acid | 10.3 | 10.5 | 1.7 |
| 2-(2-Isopropyl-indan-5-yl)-propionic acid | 7.1 | 2.5 | 1.8 |
| Acetylsalicylic acid | 133 | 81 | 194 |

Anti-inflammatory, analgesic and antipyretic activities

Pharmacological tests were effected according to the following procedures.

Anti-inflammatory activity

Tested by carrageenin edema test in rats [C. A. Winter, E. A. Risley, G. W. Nuss; J. Pharmacol. Exp. Therap., 141, 369 1963)]

Analgesic activity

Tested by thermal pain test in rats [Y. Iizuka, K. Tanaka; Folia Pharmacol. Japon, 70, 697 (1974)]

Antipyretic activity

Tested by TTG-induced fever test in guinea pigs [modified methodof S. Kobayashi, H. Takagi; Jap. J. Pharmacol., 18, 80 (1968)]

Thus, the compounds having the above formula (VI) are useful as anti-inflammatory, analgesic and antipyretic agents. For administration, there may be mentioned oral administration, for example, by tablets, capsules, granules, powders, syrups or intestinal administration by suppositories. Dosage may vary depending upon condition, age, weight and the like, but about 50 – 2000 mg is usually given for an adult per day, in one dose or several divided doses.

According to the process of this invention, the indanylpropionic acid having the formula (VI) can be prepared with a simple procedure and good yields from the compound (III) via the oxoindanylpropionic acid (I).

Thus the present invention provides a commercially advantageous process for the preparation of the indanylpropionic acid (VI).

The following examples are given for the illustration of the process for preparing the oxoindanylpropionic acid (I) and the indanylpropionic acid (VI).

EXAMPLE 1

2-(2-Isopropylindan-5-yl)propionic acid (VI)

(1) Ethyl 2-[4-(2,2-diethoxycarbonyl-3-methylbutyl)phenyl]propionate (V)

To a mixture of 8.5g. of a 50% suspension of sodium hydride in mineral oil and 180 ml. of dimethylformamide was added dropwise 70g. of diethyl isopropylmalonate at below 30° C. To the solution was added dropwise 40G. of ethyl 2-(4-chloromethylphenyl)propionate at 20° – 30° C., followed by stirring at 40° C. for 2 hours. The reaction mixture was poured into 500 ml. of ice-water, made acidic by addition of hydrochloric acid and extracted with water, dried over anhydrous sodium sulfate and evaporated to dryness. The residue was distilled under reduced pressure to give 41g. of the desired product boiling at 159° – 160° C./0.005 mmHg as a colorless oil.

Analysis for $C_{22}H_{32}O_6$ Calcd. (%): C, 67.32; H, 8.22. Found (%): C, 67.82; H, 8.47.

(2) 2-[4-(2-Carboxy-3-methylbutyl)phenyl]propionic acid (II)

To a mixture of 80g. of potassium hydroxide and 80 ml. of water was added dropwise 40.8g. of ethyl 2-[4-(2,2-diethoxycarbonyl-3-methylbutyl)phenyl]-propionate at 105° C. and the mixture was refluxed for 7 hours. After cooling, the mixture was washed with ether, made acidic by addition of conc. hydrochloric acid and extracted with ether. The extract was washed with water and an aqueous sodium chloride solution respectively, dried over anhydrous sodium sulfate and evaporated to dryness. The residue was heated under reduced pressure of 15 mmHg. at 180°–200° C. for one hour to give 26g. of the desired product as pale yellow semi-solid.

(3) 2-(2-Isopropyl-1-oxoindan-6-yl)propionic acid (I)

To 120 ml. of conc. sulfuric acid was added 26g. of 2-[4-(2-carboxy-3-methylbutyl)phenyl]propionic acid and the mixture was heated at 100° C. for 3 hours. The mixture was poured into ice-water and extracted with ether. The extract was washed with water, dried over anhydrous sodium sulfate and evaporated to dryness. The residue was subjected to vacuum distillation to give 15.7g. of the desired product boiling at 184° C./0.002 mmHg. as a colorless oil.

Analysis for $C_{15}H_{18}O_3$ Calcd. (%): C, 73.14; H, 7.37. Found (%): C, 73.08; H, 7.51.

The corresponding morpholine salt: m.p. 130° – 132° C.

(4) 2-(2-Isopropylindan-5yl)propionic acid (VI)

a. A mixture of 15g. of 2-(2-isopropyl-1-oxoindan-6-yl)propionic acid, 40g. of zinc amalgam, 50 ml. of conc. hydrochloride acid, 200 ml. of dioxane and 30 ml. of water was heated under reflux for 15 hours. After completion of the reaction, the reaction mixture was extracted with ether and the ether extract was washed with water and dried over anhydrous sodium sulfate. The solvent was distilled off from the extract and the residue was recrystallized from n-hexane to give 9.5g. of the desired product as colorless crystals of m.p. 90° – 91.5° C.

Analysis for $C_{15}H_{20}O_2$ Calcd. (%): C, 77.55; H, 8.68. Found (%): C, 77.62; H, 8.73.

Aluminum bis[2-(2-isopropylindan-5-yl)propionate]

To 30 ml. of toluene were added 2.32g. of 2-(2-isopropylindan-5-yl)propionic acid and 1.02g. of aluminum isopropoxide and the resulting mixture was heated under reflux for 3 hours. Thereafter, 10 ml. of water and 20 ml. of isopropanol were added thereto and the resulting mixture was heated under reflux for further 1.5 hours. After completion of the reaction, the solvent was distilled off under reduced pressure and to the residue was added 30 ml. of ethanol. The precipitates thus separated were recovered by filtration to give 2.2g. of the desired product as white crystals.

Analysis of $C_{30}H_{39}O_5Al.H_2O$ Calcd. (%): C, 68.68; H, 7.87 Found (%): C, 68.93; H, 7.50 b. Catalytic reduction was effected at room temperature with shaking in an apparatus for catalytic reduction under atmospheric pressure, using 1g. of 2-(2-isopropyl-1-oxoindan-6-yl)propionic acid, 0.2g. of 10% palladium on carbon, 0.1 ml. of conc. sulfuric acid and 20 ml. of ethanol. After a calculated amount of hydrogen was absorbed, insolubles were filtered off from the reaction mixture and washed with ethanol. Then, the filtrated and washings were combined and the solvent was distilled off. To the resulting residue was added 20 ml. of water followed by extraction with ether. The ether extract was washed with water and dried over anhydrous sodium sulfate. The solvent was distilled off from the extract and the residue was recrystallized from n-hexane to give 0.7g. of the desired product as colorless crystals of m.p. 90° – 91.5° C. The crystal did not show any melting point depression in a mixed melting point test with the product of the above Example 1-(4) (a) and also it coincided in its infrared spectrum completely with the above product.

EXAMPLE 2

2-(2-Ethylindan-5-yl)propionic acid (VI)

(1) Ethyl 2-[4-(2,2-diethoxycarbonylbutylphenyl]-propionic (V)

To a mixture of 3.0g. of a 50% suspension of sodium hydried in mineral oil and 50 ml. of dimethylformamide was added dropwise 11.3g. of diethyl ethylmalonate below 50° C. To the solution was added dropwise 11.3g. of ethyl 2-(4-chloromethylphenyl)propionate at 20° – 30° C., followed by stirring at 70° C. for 2 hours. The mixture was treated with the same procedure as in Example 1 (1) to give 14.4g. of the desired product boiling at 140° – 146° C./0.02 mmHg. as a pale yellow oil.

Analysis for $C_{21}H_{30}O_6$ Calcd. (%): C, 66.64; H, 7.99 Found (%): C, 66.61; H, 7.63

(2) 2-[4-(2-Carboxybutyl)phenyl]propionic acid (II)

To a mixture of 14g. of potassium hydroxide, 100 ml. of water and 10 ml. of ethanol was added 14g. of ethyl 2-[4-(2,2-diethoxycarbonylbutyl)phenyl]propionate and the mixture was refluxed for 6 hours. The reaction mixture was treated with the same procedure as in Example 1 (2) to give 11.1g. of a pale yellow oil. The oil was heated at 160° – 170° C. for 3 hours and subjected to vacuum distillation to give 7.2g. of the desired product boiling at 230° C./0.05 mmHg. as a colorless oil.

Analysis for $C_{14}H_{18}O_4$ Calcd. (%): C, 67.18; H, 7.25. Found (%): C, 67.03; H, 7.37.

(3) 2-(2-Ethyl-1-oxoindan-6yl)propionic acid (I)

To 35 ml. of conc. acid was added 7 g. of 2-[4-(2-carboxybutyl)phenyl]propionic acid and the mixture was heated at 100° C. for 1 hour. The reaction mixture was treated with the same procedure as in Example 1 (3) to give 4.1 g. of the desired product boiling at 197° – 200° C./0.15 mmHg. as a colorless oil.

Analysis for $C_{14}H_{16}O_3$ Calcd. (%): C, 72.39; H, 6.94. Found (%): C, 72.32; H, 7.10.

The corresponding piperidine salt: m.p. 85° – 86° C.

(4) 2-(2-Ethylindan-5-yl)propionic acid (VI)

A mixture of 10.5g. of 2-(2ethyl-1-oxoindan-6-yl)propionic acid, 20g. of zinc amalgam, 30 ml. of conc. hydrochloric acid, 150 ml. of dioxane and 20 ml. of water was heated under reflux for 15 hours. After completion of the reaction, the reaction mixture was extracted with ether and the ether extract was washed with water and dried over anhydrous sodium sulfate. The solvent was distilled off from the extract and the residue was subjected to vacuum distillation to give 8.2g. of the desired product as a colorless oily substance of b.p. 165° – 166° C./1.5 mmHg.

Analysis for $C_{14}H_{18}O_2$ Calcd. (%): C, 77.03; H, 8.31. Found (%); C, 76.95; H, 8.35.

2-(2-Ethylindan-5-yl)propionic acid.piperidine salt

In 2 ml. of benzene was dissolved 360mg. of 2-(2-ethylindan-5-yl)propionic acid and to the solution was added 200mg. of piperidine. The solvent was distilled off under reduced pressure and the residue was cooled to give 300mg. of a white powder. The powder was recrystallized from a mixture of chloroform and petroleum ether to give the desired product as colorless prisms of m.p. 95° – 96° C. (with decomp.).

Analysis for $C_{19}H_{29}O_2N$ Calcd. (%): C, 75.20; H, 9.63; N, 4.62. Found (%): C, 74.70; H, 9.89; N, 4.83.

Sodium 2-(2-ethylindan-5-yl)propionate

To 12.2g. of 2-(2-ethylindan-5-yl)propionic acid was added a solution of 2.2g. of sodium hydroxide in 9 ml. of water and 21 ml. of ethanol. After complete dissolution, the solvent was distilled off under reduced pressure and to the residue was added ether. The precipitates thus separated were recovered by filtration and washed with either to give 12.9g. of a white powder. The powder was recrystallized from a mixture of ethanol and ether to give the desired product as white needles of m.p. 178° – 181° C.

Analysis for $C_{14}H_{17}O_2Na$ Calcd. (%): C, 69.98; H, 7.13. Found (%): C, 70.33; H, 7.29.

What is claimed is:

1. An oxoindanylpropionic acid having the formula

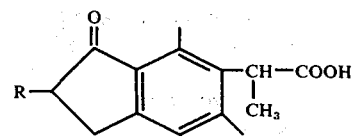

wherein R represents ethyl or isopropyl and a salt thereof.

2. 2-(2-Ethyl-1-oxoindan-6-yl)propionic acid.
3. 2-(2-Isopropyl-1-oxoindan-6-yl)propionic acid.
4. The morpholine salt of the acid of claim 3.
5. The piperidine salt of the acid of claim 2.

UNITED STATES PATENT OFFICE
CERTIFICATE OF CORRECTION

Patent No. 4,007,179            Dated February 8, 1977

Inventor(s) Norio Yoshida et al.

It is certified that error appears in the above-identified patent and that said Letters Patent are hereby corrected as shown below:

Column 2, line 52:  replace "chlorine a" with
    --- a chlorine ---.

Column 4, line 25:  replace "atmospheric" with
    --- atmospheres ---.

Column 5, line 22:  before "1963)" insert --- ( ---.

Column 7, line 20:  after "diethoxycarbonylbutyl" and
    before "phenyl", insert --- ) ---.

Column 7, line 22:  replace "hydried" with --- hydride ---.

UNITED STATES PATENT OFFICE
CERTIFICATE OF CORRECTION

Patent No. 4,007,179        Dated February 8, 1977

Inventor(s) Norio Yoshida et al.

It is certified that error appears in the above-identified patent and that said Letters Patent are hereby corrected as shown below:

Column 8, line 45: delete the formula and replace with

--- 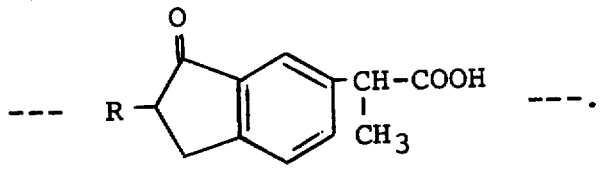 ---.

Signed and Sealed this

Thirteenth Day of September 1977

[SEAL]

Attest:

RUTH C. MASON
Attesting Officer

LUTRELLE F. PARKER
Acting Commissioner of Patents and Trademarks